United States Patent
Gigler et al.

(10) Patent No.: US 9,850,193 B2
(45) Date of Patent: Dec. 26, 2017

(54) PROCESS FOR RUTHENIUM-CATALYSED TRANSVINYLATION OF CARBOXYLIC ACIDS

(71) Applicant: WACKER CHEMIE AG, München (DE)

(72) Inventors: Peter Gigler, Dachau (DE); Jürgen Stohrer, Pullach (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/039,066

(22) PCT Filed: Nov. 19, 2014

(86) PCT No.: PCT/EP2014/075013
§ 371 (c)(1),
(2) Date: May 25, 2016

(87) PCT Pub. No.: WO2015/078746
PCT Pub. Date: Jun. 4, 2015

(65) Prior Publication Data
US 2017/0158600 A1    Jun. 8, 2017

(30) Foreign Application Priority Data
Nov. 29, 2013    (DE) .......................... 10 2013 224 491

(51) Int. Cl.
C07C 67/10    (2006.01)
C07C 67/54    (2006.01)
B01J 31/22    (2006.01)

(52) U.S. Cl.
CPC .............. *C07C 67/10* (2013.01); *C07C 67/54* (2013.01); *B01J 31/2208* (2013.01); *B01J 2531/821* (2013.01)

(58) Field of Classification Search
None
See application file for complete search history.

(56) References Cited

U.S. PATENT DOCUMENTS 4,981,973 A    1/1991    Murray
5,155,253 A *  10/1992    Murray ................... C07C 41/14
                                                              560/1

(Continued)

FOREIGN PATENT DOCUMENTS

EP    376075 A2    7/1990
WO    9209554 A1    6/1992

(Continued)

OTHER PUBLICATIONS

Written Opinion for PCT/EP2014/075013, dated Apr. 28, 2015.

*Primary Examiner* — Yate K Cutliff
(74) *Attorney, Agent, or Firm* — RatnerPrestia

(57) ABSTRACT

A process for selective transvinylation of a reactant carboxylic acid with a reactant vinyl ester to give a product vinyl ester and the corresponding acid of the reactant vinyl ester in the presence of one or more ruthenium catalysts, wherein a) the reactant vinyl ester, the reactant carboxylic acid and the ruthenium catalyst are supplied to a reactor, and b) the transvinylation reaction is conducted, wherein c) the transvinylation reaction is conducted at a conversion of more than 50%, d) on completion of the transvinylation reaction, the reactant vinyl ester and the corresponding acid are separated from the reaction mixture by distillation, e) the product vinyl ester is separated by distillation from the bottom product of the distillation, and f) the remaining reaction mixture is recycled into the reactor.

12 Claims, 1 Drawing Sheet

(56) References Cited

U.S. PATENT DOCUMENTS

| | | | |
|---|---|---|---|
| 5,210,207 A | | 5/1993 | Murray |
| 5,214,172 A | * | 5/1993 | Waller .................... C07C 67/10 554/165 |
| 9,174,921 B2 | | 11/2015 | Johnen |
| 9,174,922 B2 | | 11/2015 | Geisel |
| 2011/0275852 A1 | | 11/2011 | Meilchen |

FOREIGN PATENT DOCUMENTS

| | | |
|---|---|---|
| WO | 2011139360 A1 | 11/2011 |
| WO | 2011139361 A1 | 11/2011 |
| WO | 2013117294 A1 | 8/2013 |
| WO | 2013117295 A1 | 8/2013 |

\* cited by examiner

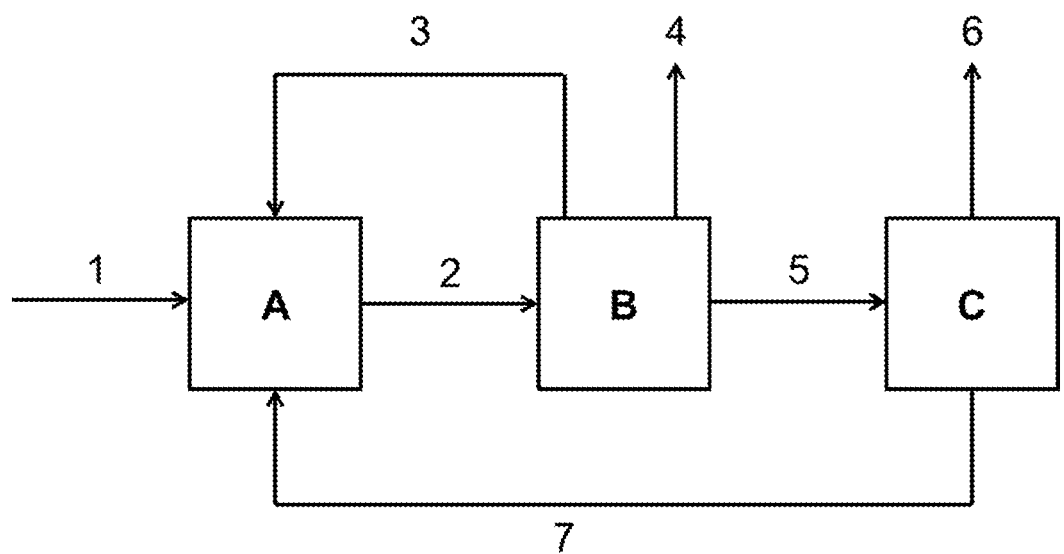

PROCESS FOR RUTHENIUM-CATALYSED TRANSVINYLATION OF CARBOXYLIC ACIDS

CROSS-REFERENCE TO RELATED APPLICATIONS

This application is the U.S. National stage filing of International Application No. PCT/EP2014/075013, filed 19 Nov. 2014, and claims priority of German application number 10 2013 224 491.6, filed 29 Nov. 2013, the entireties of which applications are incorporated herein by reference.

FIELD OF THE INVENTION

The invention relates to a process for selective transvinylation of a reactant carboxylic acid with a reactant vinyl ester to give a product vinyl ester and the corresponding acid of the reactant vinyl ester in the presence of one or more ruthenium catalysts.

BACKGROUND OF THE INVENTION

The transvinylation of carboxylic acids serves to produce vinyl esters. This is understood to mean the transfer of a vinyl unit of a reactant vinyl ester (1V) to a reactant carboxylic acid (2S) to generate a product vinyl ester (2V) and the corresponding acid of the reactant vinyl ester (1S).

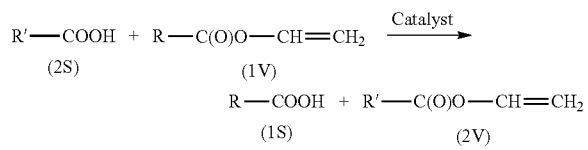

The transvinylation of vinyl esters with carboxylic acids in the presence of palladium catalyst is known from EP 376075 B1, in which copper bromide and especially lithium compounds are used as cocatalysts.

In addition to palladium catalysts and mercury catalysts, ruthenium compounds are also used as catalyst in the prior art for transvinylation of vinyl esters with carboxylic acids. Ruthenium compounds are characterized by their high solubility, low volatility and high thermal stability. In addition, they have high, temperature-inducible activity. However, a problem in using ruthenium compounds, as catalysts in the transvinylation of vinyl esters with carboxylic acids, is the formation of carboxylic anhydride as a side reaction of the transvinylation. This side reaction reduces the selectivity of the reaction. In addition, the anhydrides of the reactant carboxylic acid are relatively high boiling by-products which can only be removed from the catalyst-containing reaction mass with considerable effort and therefore would accumulate on reuse thereof.

A process for transvinylation of carboxylic acids using various Ru compounds as catalyst is described in EP 351603 A2 (U.S. Pat. No. 4,981,973). In order to shift the equilibrium, it is recommended to remove one of the reaction products continuously from the reaction mixture. In the presence of water, increasing the concentration of catalyst is recommended. For instance, in Example 60 at a water content of 2%, a ten-fold higher catalyst concentration is used than in the anhydrous case. On completion of the transvinylation, the product mixture is separated by distillation. The recycling of the Ru catalyst is not described.

EP 497340 A2 (U.S. Pat. No. 5,210,207) describes a transvinylation process for preparing product vinyl esters whose boiling points are higher than that of the reactant vinyl esters. By reactive distillation of at least one of the product components, the reaction equilibrium is shifted to the product side. The distilled reactant vinyl ester is at the same time recycled into the reaction. The formation of anhydrides as by-product is described when using Ru catalysts. Their formation is favored by high reaction temperature, high degree of conversion, long residence time and by a high concentration of reactants. For maximum selectivity and minimizing anhydride formation the authors recommend the reaction to be conducted as far as possible at a low degree of conversion and low residence time. The reuse of an Ru-containing catalyst under such conditions is described in Example 3. Here, neodecanoic acid is transvinylated at a conversion of only 50%. The reuse of an Ru-containing reaction bottoms after a reaction with a high degree of conversion is not described.

A process is described in WO 92/09554 A1 in which the reaction mass of reactant carboxylic acid and catalyst is separated in a first step after the transvinylation and the product vinyl ester is subsequently separated by azeotropic distillation. This process is especially aimed at the separation of acid/vinyl ester mixtures having small boiling point differences. The transvinylation itself is operated continuously. Only reactant vinyl ester and a mixture of catalyst and reactant carboxylic acid are continuously fed back to the reactor. The formation of anhydrides and also recycling thereof is not described. The examples cited imply that the Ru-catalyzed transvinylations were deliberately conducted at low conversions in order to avoid the formation of anhydride.

On account of the problem already described when using Ru catalyst, the low selectivity due to anhydride formation, the process is predominantly operated using palladium catalysts in the specifically disclosed embodiments in the more recent publications of the prior art. WO 2011/139360 A1 (US20110275852) describes a continuous process for preparing carboxylic vinyl esters by reactive distillation. In this case, vinyl acetate as reactant vinyl ester and the acetic acid resulting therefrom are distilled off continuously, wherein the vinyl acetate is recycled into the process. Exclusively Pd-catalyzed systems are given in the examples which are characterized by high selectivity and form no anhydrides. The Ru-catalyzed transvinylation at high conversions with subsequent recycling of the catalyst is not described. WO 2011/139361 A1 describes a very similar process, the only difference being that the transvinylation is not conducted continuously but semi-continuously.

WO 2013/117294 A1 describes a continuous process for preparing carboxylic vinyl esters. In contrast to the reactive distillation processes just discussed, the transition metal-catalyzed transvinylation is operated in the steady-state and the reaction mixture is separated in a subsequent step. WO 2013/117295 A1 describes a further configuration of this process with a subsequent derivatization of the resulting conjugate acid of the reactant vinyl ester. In both documents, the low yield and selectivity of Ru-catalyzed transvinylations and a conversion-limited mode of operation for suppression of anhydride formation are referred to. The reuse of an Ru-containing catalyst after a transvinylation at high conversion is not described in the examples of both documents.

The use of Ru catalysts in the transvinylation reaction has distinct advantages compared to Pd catalysts with respect to solubility, volatility, thermal stability and thermally inducible activity. The significant occurrence of anhydride formation, in contrast to Pd catalysis, is described in the prior art as a major disadvantage of these systems, which significantly degrades the selectivity of the process and thus the possibility of reusing the catalyst.

SUMMARY OF THE INVENTION

The object, therefore, consists of developing a process for transvinylation which is characterized by a high selectivity at simultaneously high conversion.

The invention provides a process for selective transvinylation of a reactant carboxylic acid with a reactant vinyl ester to give a product vinyl ester and the corresponding acid of the reactant vinyl ester in the presence of one or more ruthenium catalysts, wherein a) the reactant vinyl ester, the reactant carboxylic acid and the ruthenium catalyst are supplied to a reactor, and b) the transvinylation reaction is conducted, characterized in that c) the transvinylation reaction is conducted at a conversion of more than 50%, d) on completion of the transvinylation reaction, the reactant vinyl ester and the corresponding acid are removed from the reaction mixture by distillation, e) the product vinyl ester is separated by distillation from the bottom product of the distillation, and f) the remaining reaction mixture is recycled into the reactor.

BRIEF DESCRIPTION OF THE DRAWING

The drawing is a schematic diagram depicting a process for ruthenium-catalysed transvinylation of carboxylic acids according to the invention.

DETAILED DESCRIPTION OF THE INVENTION

The fundamental operation of the process according to the invention is shown in the drawing. The reactants (1) are fed individually or as a mixture to a reactor (A). The transvinylation reaction takes place in reactor (A). The resulting reaction mixture (2) is freed from reactant vinyl ester (3) and its corresponding acid (4) in a distillation apparatus (B). The reactant vinyl ester (3) is optionally recycled to reactor (A). From the remaining product mixture (5), the product vinyl ester (6) is subsequently separated partly or completely in a distillation apparatus (C). The residual catalyst-containing reaction bottoms (7) is fed back into reactor (A) and the catalyst is therefore reused.

Stirred tank, stirred tank cascades or tubular reactors may be used as reactor (A). Reactor (A) is preferably a tubular reactor.

Any carboxylic vinyl ester of the general formula R—C(O)O—CH=$CH_2$ may be used as reactant vinyl ester, where R can be an aliphatic residue having 1 to 12 carbon atoms, or can be a cycloaliphatic residue having up to 12 carbon atoms, or can be an aromatic residue having up to 12 carbon atoms. Preference is given to using low molecular weight reactant vinyl esters where R is an alkyl residue having 1 to 6 carbon atoms. Particular preference is given to using vinyl acetate.

Furthermore, at least one reactant carboxylic acid of the general formula R'—COOH is fed back to the reactor, where R' can be an aliphatic residue having 1 to 22 carbon atoms, or can be a cycloaliphatic residue having up to 22 carbon atoms, or can be an aromatic residue having up to 22 carbon atoms. Preference is given to using reactant carboxylic acids of the compound classes mentioned having 6 to 18 carbon atoms. Examples of these are caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid and naphthalenecar-boxylic acid. Particular preference is given to versatic acids$^R$ (alpha-branched carboxylic acids having 9 to 12 carbon atoms from Momentive) or neo acids having 9 to 12 carbon atoms and fatty acids such as lauric acid, myristic acid, palmitic acid and stearic acid.

Ruthenium compounds suitable as catalyst are known to those skilled in the art, for example, from U.S. Pat. No. 4,981,973 of which the disclosure is incorporated here by way of reference. Suitable ruthenium compounds are, for example, ruthenium carbonyl compounds and ruthenium carboxylate compounds. Further ruthenium compounds which give rise to highly active catalysts are ruthenium(III) acetylacetonate, ruthenium(IV) oxide, ruthenium on supports such as carbon or aluminum oxide, ruthenium halides such as Ru(III) chloride and Ru(III) iodide.

The Ru catalyst is typically used at concentrations of 0.1 to 10 000 ppm (ruthenium content based on the reaction mass of reactant vinyl ester and reactant carboxylic acid), preference being given to the use of 1 to 1000 ppm (ruthenium content based on the reaction mass of reactant vinyl ester and reactant carboxylic acid).

Optionally, a polymerization inhibitor can be added to the reactants. Preference is given to using 100 to 10 000 ppm polymerization inhibitor, based on the reaction mass of reactant vinyl ester and reactant carboxylic acid. Examples of polymerization inhibitors are hydroquinone, methoxyhydroquinone, tertiary-butyl catechol, phenothiazine or nitroxide radicals such as TEMPO or 4-OH-TEMPO (TEMPO=2,2,6,6-tetramethylpiperidinyloxyl). Preference is given to the use of phenothiazine or hydroquinone.

An anhydride of the respective reactant carboxylic acid may also optionally be added as reactant. The optionally supplied anhydrides of the reactant carboxylic acid of the general formula $R^1$—C(O)—O—C(O)—$R^2$ may be present as mixed ($R^1 \neq R^2$) or symmetrical ($R^1=R^2$) anhydrides, where $R^1$ and $R^2$ is in each case an aliphatic residue having 1 to 22 carbon atoms, or a cycloaliphatic residue having up to 22 carbon atoms or an aromatic residue having up to 22 carbon atoms. Examples of these are mixed or symmetrical anhydrides of the following acids: acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid and naphthalenecar-boxylic acid. Preference is given to the use of the symmetrical anhydrides of the reactant carboxylic acid.

For the transvinylation, the reactant vinyl ester, reactant carboxylic acid and Ru catalyst reactants, and also optionally inhibitor and optionally anhydride of the reactant carboxylic acid, can be supplied to the reactor individually or in a mixture.

The molar ratio of reactant vinyl ester to reactant carboxylic acid can be 1:10 to 10:1. Preference is given to a ratio of reactant vinyl ester to reactant carboxylic acid of 2:1 to 8:1, particular preference being given to a ratio of 3:1 to 6:1.

The transvinylation is generally carried out at a temperature of 100° C. to 170° C., preferably at a temperature of 120° C. to 150° C. The pressure at which the transvinylation is conducted is dependent on the temperature and is generally ≥2 bar abs., preferably 5 to 15 bar abs., and most preferably 5 to 10 bar abs. The reaction is preferably conducted in a protective gas atmosphere, nitrogen for example, in a manner known per se.

The residence time in the reactor in the process according to the invention is generally 0.25 to 5 hours, preferably 1 hour to 4 hours.

The reaction is conducted at a conversion of more than 50%, preferably from 60% to 90%, particularly preferably from 65% to 80%, most preferably from 70% to 80%, based in each case on the starting component, reactant vinyl ester or reactant carboxylic acid, present in the lower molar proportion. The conversion U is defined as U (%)=100×($n_0$−$n_E$)/$n_0$, where $n_0$ is the amount of the respective starting component at the start of the reaction and $n_E$ is the amount thereof in each case at the end of the reaction. The conversion may be adjusted, in each case in a manner known to those skilled in the art, by the molar ratio of reactant vinyl ester to reactant carboxylic acid, the residence time, the temperature or the concentration of catalyst.

In contrast to a reactive distillation, the separation of the product mixture obtained in the process according to the invention is carried out only after completion of the transvinylation, preferably by means of distillation in appropriate distillation columns. Pressure and temperature of the distillation and the design of the distillation columns depend on the components present in the product mixture and may be determined, for example, by means of routine experiments by those skilled in the art. In the process according to the invention, no azeotropic distillation is conducted.

In the separation of the product mixture, in a first step the unreacted residue of the reactant vinyl ester and corresponding acid thereof are both removed from the product mixture. The reactant vinyl ester resulting therefrom can optionally be fed back into the reactor for renewed transvinylation. The corresponding acid of the reactant vinyl ester resulting therefrom can be used as reactant in other chemical processes; in the case of acetic acid, for example, for producing vinyl acetate.

For the further work-up of the product mixture remaining thereafter, various routes can be pursued:

In a first embodiment, the product vinyl ester is at least partly or completely separated by distillation from the remaining product mixture after removal of the reactant vinyl ester and corresponding acid thereof. The resulting reaction bottoms, which may comprise reactant carboxylic acid, anhydrides of the reactant carboxylic acid, ruthenium catalyst and optionally further components such as product vinyl ester or polymeric constituents, is fed back into the reactor for renewed transvinylation on addition of fresh reactants and optionally fresh catalyst.

In an alternative embodiment, the product vinyl ester is likewise at least partly or completely separated by distillation from the remaining product mixture after removal of the reactant vinyl ester and corresponding acid thereof. After separation of the product vinyl ester, water is added to the resulting reaction bottoms. The amount of water added is preferably 1 to 5 mol equivalents, based on the amount of anhydride of the reactant carboxylic acid present in the reaction bottoms. Particular preference is given to adding about one equivalent of water per equivalent of anhydride of the reactant carboxylic acid. Subsequently, the reaction bottoms is treated such that the anhydride of the reactant carboxylic acid is completely hydrolyzed, preferably to at least 80 mol %. For this purpose, a temperature of 40° C. to 160° C., preferably 100° C. to 140° C., is set. The hydrolysis is carried out over a period of 1 to 30 minutes, preferably 1 to 10 minutes. The reaction bottoms obtained after hydrolysis of the anhydride of the reactant carboxylic acid, which may comprise reactant carboxylic acid, Ru catalyst and optionally further components such as product vinyl ester or polymeric constituents, is fed back into the reactor for renewed transvinylation on addition of fresh reactants and optionally fresh catalyst.

In a further embodiment, water is added in a first step to the remaining product mixture after removal of the reactant vinyl ester and corresponding acid thereof. The amount of water added is preferably 1 to 5 mol equivalents, based on the amount of anhydride of the reactant carboxylic acid present in the reaction bottoms. Particular preference is given to adding about one equivalent of water per anhydride of the reactant carboxylic acid. Subsequently, the reaction bottoms is treated such that the anhydride of the reactant carboxylic acid is completely hydrolyzed, preferably to at least 80 mol %. For this purpose, a temperature of 40° C. to 160° C., preferably of 100° C. to 140° C., is set. The hydrolysis is carried out over a period of 1 to 30 minutes, preferably 1 to 10 minutes. Subsequently, the product vinyl ester is at least partly or completely separated by means of distillation. The reaction bottoms obtained after distillation of the product vinyl ester, which may comprise reactant carboxylic acid, Ru catalyst and optionally further components such as product vinyl ester or polymeric constituents, is fed back into the reactor for renewed transvinylation on addition of fresh reactants and optionally fresh catalyst.

Fresh reactants and optionally fresh catalyst can be added to the reactor for renewed transvinylation either in a mixture with the recycled reaction bottoms or separately from the recycled reaction bottoms.

Polymeric constituents present in the product mixture can be optionally partly or completely removed. The polymeric constituents can be removed, for example, by filtration, extraction, sedimentation or precipitation, preference being given to removal by precipitation, sedimentation or filtration. The removal can be carried out before or only after addition of water. The removal is effected with recovery of the Ru catalyst such that the polymeric constituents removed have a lower mass of ruthenium than the reaction bottoms (7) recycled into the reactor (A).

The substeps of the process, both the transvinylation and the work-up steps, may be carried out batchwise, semi-continuously and in non-stop mode. The process is preferably carried out in non-stop mode.

Using the process according to the invention, even at high conversions, high selectivities can be achieved. The selectivity of the transvinylation reaction is preferably ≥95%, particularly preferably ≥97%, most preferably ≥99%. The selectivity refers to the yield Y of product vinyl ester per reacted starting component, according to S=Y/R. The yield is calculated according to Y (%)=100×($p_E$−$p_0$)/$n_0$, where $p_E$ is the amount of product vinyl ester obtained after the reaction, $p_0$ is the amount of product vinyl ester at the start of the reaction (present in the reused catalyst-containing reaction bottoms) and $n_0$ is the amount of the starting component used in the lower molar proportion.

Accumulation of carboxylic anhydride by repeated recycling of catalyst and reaction bottoms comprising anhydrides of the reactant carboxylic acid was surprisingly not observed. It has been found, surprisingly, that carboxylic anhydrides in the Ru catalysed transvinylation reaction can be converted to product vinyl esters.

Furthermore, the carboxylic anhydride can be hydrolyzed by addition of water. It has been found, surprisingly, that even on addition of relatively large amounts of water to the Ru containing reaction bottoms, the activity of the catalyst when reused for the transvinylation is not impaired.

The process according to the invention therefore enables an economic method of transvinylation in which the Ru catalyst can be used repeatedly by recycling of the reaction bottoms.

EXAMPLES

The following examples serve to illustrate the invention in detail.

The conversions stated refer in all cases to the starting component, reactant carboxylic acid (2S) or reactant vinyl ester (1V), used at the lower molar proportion. The conversion C is defined as $C(\%)=100\times(n_0-n_E)/n_0$, where $n_0$ is the amount of starting component at the start of the reaction and $n_E$ is the amount at the end of the reaction.

Stated selectivities S refer to the yield Y of product vinyl ester per reacted starting component, according to $S=Y/R$. The yield is calculated according to $Y(\%)=100\times(p_E-p_0)/n_0$, where $p_E$ is the amount of product vinyl ester obtained after the reaction, $p_0$ is the amount of product vinyl ester at the start of the reaction (present in the reused catalyst-containing reaction bottoms) and $n_0$ is the amount of the starting component used in the lower molar proportion.

Example 1

Transvinylation at high conversion and high selectivity with recycling of the anhydride-containing reaction bottoms.

In a 100 ml Berghof autoclave, 23.2 g of lauric acid, 29.9 g of vinyl acetate and 0.074 g of triruthenium dodecacarbonyl at 4 bar abs. were heated to 140° C. for 1 hour. After cooling, acetic acid and vinyl acetate were removed on a rotary evaporator and vinyl laurate was distilled under reduced pressure. The residue of lauric anhydride, lauric acid and Ru catalyst was reused under identical conditions after addition of fresh lauric acid and fresh vinyl acetate.

After each cycle, the molar proportions in the reaction mixture required for the calculation of conversion and selectivity were determined by means of quantitative NMR spectroscopy.

| Cycle | | Molar proportions | | Conversion | Selectivity Vinyl |
|---|---|---|---|---|---|
| | | Lauric acid | Vinyl laurate | Lauric anhydride | Lauric acid [%] | laurate [%] |
| 1 | Start | 0.996 | 0.004 | 0.000 | | |
| | End | 0.253 | 0.741 | 0.006 | 74.6 | 99.2 |
| 2 | Start | 0.932 | 0.053 | 0.015 | | |
| | End | 0.223 | 0.759 | 0.018 | 76.1 | 99.5 |
| 3 | Start | 0.899 | 0.023 | 0.078 | | |
| | End | 0.233 | 0.735 | 0.032 | 74.1 | 106.9 |
| 4 | Start | 0.910 | 0.008 | 0.083 | | |
| | End | 0.240 | 0.733 | 0.027 | 73.6 | 108.3 |
| 5 | Start | 0.913 | 0.028 | 0.058 | | |
| | End | 0.249 | 0.729 | 0.022 | 72.8 | 105.4 |

The example shows that, on reusing catalyst-containing reaction bottoms, after an initial increase, no further accumulation of lauric anhydride occurs. Furthermore, it is evident that the proportion of anhydride increases by the distillative work-up, which is between the end of the reaction of one cycle and the start of the next cycle. Some of this anhydride is also converted in the following cycle to vinyl laurate, from which arithmetical selectivities greater than 100% are obtained.

Example 2

Transvinylation of lauric anhydride 25 g of lauric anhydride and 454 ppm Ru in the form of a catalyst-containing reaction bottoms were initially charged in a 100 ml Berghof autoclave and heated at 6 bar abs. to 140° C. At this temperature, 45 g of vinyl acetate were added. Subsequently, the composition of the reaction mixture over the time course was investigated by NMR spectroscopy.

| Time | Conversion [%] | Yield [%] Vinyl laurate | Selectivity [%] |
|---|---|---|---|
| 10 min | 18.5 | 11.4 | 62 |
| 20 min | 27.4 | 21.1 | 77 |
| 30 min | 34.4 | 28.7 | 83 |
| 45 min | 40.1 | 35.1 | 88 |
| 60 min | 45.7 | 41.9 | 92 |
| 90 min | 54.0 | 50.5 | 94 |
| 120 min | 60.2 | 57.2 | 95 |

The example demonstrates that lauric anhydride was also converted under the stated conditions to vinyl laurate. In the steady-state, the conversion here is also higher than 60%.

Example 3

Transvinylation at high conversion and high selectivity with recycling of the reaction bottoms after addition of water (vinyl laurate separation before addition of water)

In a 100 ml Berghof autoclave, 32.5 g of lauric acid, 41.9 g of vinyl acetate and 0.10 g of triruthenium dodecacarbonyl at 4 bar abs. were heated to 140° C. for 1 hour. After cooling, acetic acid and vinyl acetate were removed on a rotary evaporator and subsequently vinyl laurate was distilled off under reduced pressure. After addition of 5% by weight water (based on the mass of the reaction bottoms) and after 5 min stirring at 140° C., the residue of lauric acid and Ru catalyst was reused for transvinylation under identical conditions after addition of fresh lauric acid and fresh vinyl acetate.

| Cycle | | Molar proportions | | | Conversion | Selectivity Vinyl |
|---|---|---|---|---|---|---|
| | | Lauric acid | Vinyl laurate | Lauric anhydride | Lauric acid [%] | laurate [%] |
| 1 | Start | 0.997 | 0.003 | 0.000 | | |
| | End | 0.226 | 0.766 | 0.008 | 77.4 | 99.0 |
| 2 | Start | 0.988 | 0.012 | 0.000 | | |
| | End | 0.221 | 0.757 | 0.021 | 77.6 | 97.2 |
| 3 | Start | 0.920 | 0.043 | 0.037 | | |
| | End | 0.217 | 0.765 | 0.018 | 76.4 | 102.8 |
| 4 | Start | 0.933 | 0.015 | 0.052 | | |
| | End | 0.210 | 0.762 | 0.028 | 77.5 | 103.4 |
| 5 | Start | 0.923 | 0.013 | 0.063 | | |
| | End | 0.212 | 0.761 | 0.026 | 77.0 | 105.2 |

Example 4

Transvinylation at high conversion and high selectivity with recycling of the reaction bottoms after addition of water (vinyl laurate separation after addition of water).

In a 100 ml Berghof autoclave, 26.9 g of lauric acid, 34.7 g of vinyl acetate and 0.086 g of triruthenium dodecacarbonyl at 4 bar abs. were heated to 140° C. for 1 hour. After cooling, acetic acid and vinyl acetate were removed on a rotary evaporator. After addition of 10% by weight water (based on the product mixture), vinyl laurate was distilled off under reduced pressure. The residue of lauric acid and Ru catalyst was reused for transvinylation under identical conditions after addition of fresh lauric acid and fresh vinyl acetate.

| Cycle | | Molar proportions | | Conversion | Selectivity Vinyl |
|---|---|---|---|---|---|
| | Lauric acid | Vinyl laurate | Lauric anhydride | Lauric acid [%] | laurate [%] |
| 1 Start | 0.996 | 0.004 | 0.000 | | |
| End | 0.253 | 0.741 | 0.006 | 74.6 | 99.2 |
| 2 Start | 0.932 | 0.022 | 0.045 | | |
| End | 0.263 | 0.720 | 0.018 | 71.8 | 104.1 |
| 3 Start | 0.936 | 0.020 | 0.044 | | |
| End | 0.276 | 0.708 | 0.016 | 70.6 | 104.2 |
| 4 Start | 0.950 | 0.013 | 0.037 | | |
| End | 0.271 | 0.716 | 0.013 | 71.5 | 103.5 |
| 5 Start | 0.946 | 0.017 | 0.037 | | |
| End | 0.261 | 0.724 | 0.015 | 72.4 | 103.2 |

Comparison of the results of Example 1 with those of Example 3 and 4 shows that the addition of water (Example 3 and 4) does not cause any inhibition of the Ru catalysis on reuse of the catalyst. Similar high values for conversion and selectivity were obtained.

Example 5

Removal of polymeric constituents from the reaction bottoms 0.34 g of polymeric constituents were removed by sedimentation from 15.6 g of an Ru-containing (0.023 g Ru) reaction bottoms comprising lauric acid, lauric anhydride, vinyl laurate and polymeric constituents. The remaining solution comprised 0.021 g of ruthenium.

The example shows that polymeric constituents can be removed without significant losses of Ru catalyst.

The invention claimed is:

1. A process for selective transvinylation of a reactant carboxylic acid with a reactant vinyl ester to give a product vinyl ester and an acid corresponding to the reactant vinyl ester, comprising the steps of
    a) performing a transvinylation reaction using a reaction mixture comprising the reactant vinyl ester, the reactant carboxylic acid, and one or more ruthenium catalysts in a reactor,
  wherein
    the transvinylation reaction is conducted at a conversion of more than 50%;
    b) removing unreacted reactant vinyl ester and the acid corresponding to the reactant vinyl ester from a product of step a) by distillation on completion of the transvinylation reaction of step a), thereby forming a bottom product;
    c) separating the product vinyl ester from the bottom product by distillation, thereby forming reaction bottoms; and
    d) recycling the reaction bottoms into the reactor.

2. The process as claimed in claim 1, further comprising adding water to the reaction bottoms and holding for a time sufficient to hydrolyze carboxylic acid anhydrides present therein before performing step d).

3. The process as claimed in claim 1, further comprising adding water to the bottom product and holding for a time sufficient to hydrolyze carboxylic acid anhydrides present therein before performing step c).

4. The process as claimed in claim 1, wherein the reactant vinyl ester is of the general formula R—C(O)O—CH=CH$_2$, where R is an aliphatic residue having 1 to 12 carbon atoms, or is a cycloaliphatic residue having up to 12 carbon atoms, or is an aromatic residue having up to 12 carbon atoms.

5. The process as claimed in claim 1, wherein the reactant vinyl ester is vinyl acetate.

6. The process as claimed in claim 1, wherein the reactant carboxylic acid is of the general formula R'—COOH, where R' is an aliphatic residue having 1 to 22 carbon atoms, or is a cycloaliphatic residue having up to 22 carbon atoms, or is an aromatic residue having up to 22 carbon atoms.

7. The process as claimed in claim 1, wherein the reactant carboxylic acid is selected from the group consisting of alpha-branched carboxylic acids having 9 to 12 carbon atoms, neo acids having 9 to 12 carbon atoms, and fatty acids.

8. The process as claimed in claim 1, further comprising adding an anhydride of the reactant carboxylic acid to the reactor.

9. The process as claimed in claim 1, further comprising partly or completely removing polymeric constituents present in the reaction mixture.

10. The process as claimed in claim 1, wherein the steps of the process are each conducted non-stop.

11. The process as claimed in claim 1, wherein the selectivity of the transvinylation reaction is ≥95%.

12. The process as claimed in claim 1, wherein the reactant carboxylic acid is selected from the group consisting of lauric acid, myristic acid, palmitic acid, and stearic acid.

* * * * *